United States Patent [19]

Guerrero et al.

[11] Patent Number: 5,505,935
[45] Date of Patent: Apr. 9, 1996

[54] SUNSCREEN COMPOSITIONS

[75] Inventors: Angel A. Guerrero, Huntington; Thomas C. Klepacky, Shelton, both of Conn.

[73] Assignee: Elizabeth Arden Company, Division of Conopco, Inc., New York, N.Y.

[21] Appl. No.: 239,660

[22] Filed: May 9, 1994

[51] Int. Cl.⁶ .................... A61K 7/021; A61K 7/40; A61K 7/42; A61K 7/44
[52] U.S. Cl. .................... 424/59; 424/60; 514/772; 514/772.3; 514/772.4; 514/844; 514/847; 514/937; 514/938
[58] Field of Search .................... 424/59

[56] References Cited

U.S. PATENT DOCUMENTS

| | | | |
|---|---|---|---|
| 3,529,055 | 9/1970 | Skoultchi et al. | 424/59 |
| 3,590,118 | 6/1971 | Conrady et al. | 424/47 |
| 4,197,316 | 4/1980 | Yu et al. | 514/459 |
| 4,597,963 | 7/1986 | Deckner | 424/59 |
| 4,810,489 | 3/1989 | Murray et al. | 424/59 |
| 4,917,883 | 4/1990 | Strobridge | 424/59 |
| 4,919,934 | 4/1990 | Deckner et al. | 424/59 |
| 5,008,100 | 4/1991 | Zecchino et al. | 424/59 |
| 5,041,281 | 8/1991 | Strobridge | 424/59 |
| 5,061,480 | 10/1991 | Marchese et al. | 424/59 |
| 5,208,011 | 5/1993 | Vaughan . | |
| 5,219,558 | 6/1993 | Woodin, Jr. et al. | 424/59 |
| 5,223,250 | 6/1993 | Mitchell et al. . | |

FOREIGN PATENT DOCUMENTS

| | | |
|---|---|---|
| 2597336 | 1/1986 | France . |
| 2172503 | 2/1986 | United Kingdom . |
| WO88/01164 | 2/1988 | WIPO . |

Primary Examiner—Shelley A. Dodson
Attorney, Agent, or Firm—Milton L. Honig

[57] ABSTRACT

A cosmetic sunscreen composition is described that includes an ethylene/vinyl acetate copolymer, an acrylic polymer such as poly(methyl methacrylate) and a chromophoric organic sunscreen agent capable of absorbing ultraviolet radiation within the range 290 to 400 nm. The ethylene/vinyl acetate copolymer and acrylic polymer have been found to interactively boost the SPF value of the organic sunscreen.

8 Claims, No Drawings

SUNSCREEN COMPOSITIONS

BACKGROUND OF THE INVENTION

1. Field of the Invention

The invention relates to sunscreen compositions, particularly those in lotion and cream form.

2. The Related Art

Sunscreen compositions are commonly used during outdoor work or leisure for protection of exposed skin against painful sunburn. Many effective sunscreen preparations are sold commercially or are described in cosmetic or pharmaceutical literature. In general, sunscreen preparations are formulated in the form of creams, lotions or oils containing as the active agent an ultraviolet radiation absorbing chemical compound. The active agent functions by blocking passage of erythematogenic radiation thereby preventing its penetration into the skin.

The ideal sunscreen formulation should be non-toxic and non-irritating to skin tissue and be capable of convenient application in a uniform continuous film. The product should be sufficiently chemically and physically stable so as to provide an acceptable shelf life upon storage. It is particularly desirable that the preparation should retain its protective effect over a prolonged period after application. Thus, the active agent when present on the skin must be resistant to chemical or photodegradation, to absorption through the skin, and to removal by perspiration, skin oil, or water. For aesthetic reasons, the product should be substantially odorless (or be capable of being scented) and be non-staining to the skin or clothing.

Sunscreen agents in the order of decreasing effectiveness may be categorized as either highly chromophoric monomeric organic compounds, inorganic compounds and minimally chromophoric polymeric organic solids.

U.S. Pat. No. 5,219,558 (Woodin, Jr. et al.) and U.S. Pat. No. 4,919,934 (Decker et al.) disclose photoprotection compositions wherein the active sunscreen agents are of the chromophoric monomeric organic compound variety. The examples feature the commercially common sunscreens such as octyl methoxycinnamate (Parsol MCX), benzophenone-3 (Oxybenzone) and octyl dimethyl PABA.

Chromophoric monomeric organic compounds are subject to certain problems. These compounds when present on the skin must be resistant to removal by perspiration, skin oils or water. Formulations containing these materials therefore require additives to ensure substantivity. Yet, even with the best additives waterproofing and rub off resistance is never fully accomplished. Another and perhaps more important problem is that of skin irritation. See U.S. Pat. No. 5,041,281 and U.S. Pat. No. 4,917,883 both to Strobridge reporting oil-in-water emulsion sunscreens waterproofed with, for instance, copolymers of ethylene and vinyl acetate. Some people are quite sensitive to organic molecules with chromophoric groups. Adverse allergic reactions can result. Therefore, it would be quite desirable to minimize the level of such compounds in any sunscreen compositions. Total replacement of chromophoric organic compounds, while desirable, is presently not feasible for high SPF compositions that also require certain types of aesthetics.

Inorganic particulate compounds such as titanium dioxide have been employed as sunscreen agents. In fact, titanium dioxide is quite popular with marketers advertising them as "natural sunscreens". The problem with inorganic particulate compounds is that high SPF values can only be achieved with high concentrations of these materials. Unfortunately, aesthetics suffer at such high concentrations. Clear formulas become opaque. High loadings also tend to form visible white films on the skin which consumers perceive negatively.

Polymeric organic particulates are a final category of materials which have found use in sunscreen formulations. U.S. Pat. No. 5,008,100 (Zecchino et al.) reports oil-in-water emulsions containing polyethylene particles as a co-active sunscreen agent along with the traditional chromophoric organic compounds. Similar to the inorganic materials, polymeric particles are limited in their sunscreen effectiveness. High amounts of such materials will have adverse effects upon the formula aesthetics.

Accordingly, it is an object of the present invention to provide a sunscreen composition that maximizes the sun protection factor but minimizes the level of chromophoric monomeric organic compound.

Another object of the present invention is to provide a sunscreen composition in the form of an oil and water emulsion that exhibits improved aesthetics when applied to the skin.

Yet another object of the present invention is to provide a sunscreen composition having a much lower human irritancy than formulas of equivalent sun protection factor.

These and other objects of the present invention will more readily become apparent from the description and examples which follow.

SUMMARY OF THE INVENTION

A sunscreen composition is provided which includes:

(i) from about 0.01 to about 10% of an ethylene/vinyl acetate copolymer;

(ii) from about 0.01 to about 10% of particles of an acrylic polymer;

(iii) from about 0.1 to about 30% of an organic sunscreen agent with a chromophoric group active within the ultraviolet radiation range from 290 to 400 nm; and (iv) from about 60 to about 99.5% of a pharmaceutically acceptable carrier.

DETAILED DESCRIPTION OF THE INVENTION

Now it has been discovered that ethylene/vinyl acetate copolymer and particles of an acrylic polymer can combine to provide a significant boost in the sun protection factor (SPF) to compositions with a chromophoric organic sunscreen agent. Although ethylene/vinyl acetate (EVA) copolymers have previously been employed in sunscreen compositions, this material has been heretofore incorporated as a thickener. EVA copolymers have also been recommended for their water-proofing capabilities. Only now has it been discovered that the copolymer can have a significant SPF boosting effect.

EVA copolymers according to the present invention are formed from ethylene monomers, i.e. $CH_2=CH_2$, and vinyl acetate monomers, i.e. $CH_3COOCH=CH_2$. The polymeric formula is $CH_3(CH_2)_x(CH_2CHOOCHCH_3)_y$. The preferred ratio of x:y is from about 20:1 to about 4:1, and more preferably from 12:1 to 6:1. The average molecular weight can range from about 2,000 to about 2,000,000. The hardness (dmn ASTMD-5) of the EVA copolymer is preferably between about 4 and about 80, most preferably about 9.5. The drop point (ASTMD3954) is preferably between about 60 and about 103° C., most preferably about 95° C. Preferably, the EVA copolymer is added to the composition in particulate form with an average particle size small enough to be readily dispersed in the emulsion's oil phase.

Levels of EVA copolymer suitable for compositions of this invention range between about 0.5 and about 10%. More preferably, the amount is between about 0.1 and about 2%, optimally between 0.2 and 0.5% by weight.

EVA copolymers are commercially obtainable from the Allied Signal Corporation, most preferably under the designation AC-400. Other useful EVA copolymers from Allied Signal are found under the designations AC-400A, AC-405, AC-4055, AC-405T and ACT-430 and from DuPont Chemical under the designation Elvox 40P.

A second critical element of compositions according to the present invention is that of an acrylic polymer. More specifically, the polymer will be a homopolymer derived from monomers including ethyl acrylate, methyl acrylate, ethyl methacrylate, methyl methacrylate, butyl acrylate and butyl methacrylate. Most preferred is poly(methyl methacrylate) commercially available as microbeads designated as Covabead PMMA from Wackherr S.A., France. Particulate sizes of the acrylic polymer will range from about 0.001 to less than 5 micron, preferably between about 0.01 and 3 micron, optimally between about 0.1 and 1 micron average particle size.

Amounts of the acrylic polymer will range from about 0.01 to about 10%, preferably from about 0.1 to about 5%, optimally between about 0.8 and 1.5% by weight.

A third essential element of compositions according to the present invention is that of an organic sunscreen agent having at least one chromophoric group absorbing within the ultraviolet range somewhere from 290 to 400 nm. Chromophoric organic sunscreen agents may be divided into the following categories (with specific examples) including:

p-Aminobenzoic acid, its salts and its derivatives (ethyl, isobutyl, glyceryl esters; p-dimethylaminobenzoic acid); Anthranilates (i.e., o-aminobenzoates; methyl, menthyl, phenyl, benzyl, phenylethyl, linalyl, terpinyl, and cyclohexenyl esters); Salicylates (octyl, amyl, phenyl, benzyl, menthyl, glyceryl, and dipropyleneglycol esters); Cinnamic acid derivatives (menthyl and benzyl esters, α-phenyl cinnamonitrile; butyl cinnamoyl pyruvate); Dihydroxycinnamic acid derivatives (umbelliferone, methylumbelliferone, methylaceto-umbelliferone); Trihydroxycinnamic acid derivatives (esculetin, methylesculetin, daphnetin, and the glucosides, esculin and daphnin); Hydrocarbons (diphenylbutadiene, stilbene); Dibenzalacetone and benzalacetophenone; Naptholsulfonates (sodium salts of 2-naphthol-3,6-disulfonic and of 2-naphthol-6,8-disulfonic acids); Dihydroxy-naphthoic acid and its salts; o- and p- Hydroxybiphenyldisulfonates; Coumarin derivatives (7-hydroxy, 7-methyl, 3-phenyl); 18 Diazoles (2-acetyl-3-bromoindazole, phenyl benzoxazole, methyl naphthoxazole, various aryl benzothiazoles); Quinine salts (bisulfate, sulfate, chloride, oleate, and tannate); Quinoline derivatives (8-hydroxyquinoline salts, 2-phenylquinoline); Hydroxy- or methoxy-substituted benzophenones; Uric and vilouric acids; Tannic acid and its derivatives (e.g., hexaethylether); (Butyl carbityl) (6-propyl piperonyl) ether; Hydroquinone; Benzophenones (Oxybenzone, Sulisobenzone, Dioxybenzone, Benzoresorcinol, 2,2', 4,4'-Tetrahydroxybenzophenone, 2,2'-Dihydroxy-4,4'-dimethoxybenzophenone, Octabenzone; 4-Isopropyldibenzoylmethane; Butylmethoxydibenzoylmethane; Etocrylene; and 4-isopropyl-dibenzoylmethane.

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[ bis(hydroxypropyl)]aminobenzoate, 2-ethylhexyl-2-cyano-3,3-diphenylacrylate, 2-ethylhexylsalicylate, glyceryl p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid 2-(p-dimethylaminophenyl)- 5-sulfoniobenzoxazoic acid and mixtures thereof.

Amounts of the aforementioned sunscreen agents will generally range from about 0.1 to about 30%, preferably from about 2 to about 20%, optimally from about 4 to about 10% by weight.

Compositions of the present invention may either be aqueous or anhydrous. Preferably the compositions are aqueous, especially water and oil emulsions of the W/O or O/W variety. Water when present will be in amounts which may range from about 5 to about 90%, preferably from about 35 to about 65%, optimally between about 40 and 50% by weight.

Besides water, relatively volatile solvents may also be incorporated within compositions of the present invention. Most preferred are monohydric $C_1$-$C_3$ alkanols. These include ethyl alcohol, methyl alcohol and isopropyl alcohol. The amount of monohydric alkanol may range from about 5 to about 50%, preferably from about 15 to about 40%, optimally between about 25 to about 35% by weight.

Emollient materials in the form of silicone oils and synthetic esters may be incorporated into compositions of the present invention. Amounts of the emollients may range anywhere from about 0.1 to about 30%, preferably between about 1 and 20% by weight.

Silicone oils may be divided into the volatile and nonvolatile variety. The term "volatile" as used herein refers to those materials which have a measurable vapor pressure at ambient temperature. Volatile silicone oils are preferably chosen from cyclic or linear polydimethylsiloxanes containing from about 3 to about 9, preferably from about 4 to about 5, silicon atoms.

Linear volatile silicone materials generally have viscosities less than about 5 centistokes at 25° C. while cyclic materials typically have viscosities of less than about 10 centistokes.

Nonvolatile silicone oils useful as an emollient material include polyalkyl siloxanes, polyalkylaryl siloxanes and polyether siloxane copolymers. The essentially non-volatile polyalkyl siloxanes useful herein include, for example, polydimethyl siloxanes with viscosities of from about 5 to about 100,000 centistokes at 25° C. Among the preferred non-volatile emollients useful in the present compositions are the polydimethyl siloxanes having viscosities from about 10 to about 400 centistokes at 25° C.

Among the ester emollients are:

(1) Alkenyl or alkyl esters of fatty acids having 10 to 20 carbon atoms. Examples thereof include isononyl isonanonoate, oleyl myristate, oleyl stearate, and oleyl oleate.

(2) Ether-esters such as fatty acid esters of ethoxylated fatty alcohols.

(3) Polyhydric alcohol esters. Ethylene glycol mono and di-fatty acid esters, diethylene glycol mono- and di-fatty acid esters, polyethylene glycol (200–6000) mono- and di-fatty acid esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters.

(4) Wax esters such as beeswax, spermaceti, myristyl myristate, stearyl stearate.

(5) Sterols esters, of which cholesterol fatty acid esters are examples thereof.

The most preferred esters are octyldodecyl neopentanoate (available as Elefac I-205®) and isononyl isononanoate.

Fatty acids having from 10 to 30 carbon atoms may also be included in the compositions of this invention. Illustrative of this category are pelargonic, lauric, myristic, palmitic, stearic, isostearic, hydroxystearic, oleic, linoleic, ricinoleic, arachidic, behenic and erucic acids.

Humectants of the polyhydric alcohol-type may also be included in the compositions of this invention. The humectant aids in increasing the effectiveness of the emollient, reduces scaling, stimulates removal of built-up scale and improves skin feel. Typical polyhydric alcohols include glycerol, polyalkylene glycols and more preferably alkylene polyols and their derivatives, including propylene glycol, dipropylene glycol, polypropylene glycol, polyethylene glycol and derivatives thereof, sorbitol, hydroxypropyl sorbitol, hexylene glycol, 1,3-butylene glycol, 1,2,6-hexanetriol, ethoxylated glycerol, propoxylated glycerol and mixtures thereof. For best results the humectant is preferably propylene glycol. The amount of humectant may range anywhere from 0.5 to 30%, preferably between 1 and 15% by weight of the composition.

Thickeners/viscosifiers in amounts from about 0.01 to about 5% by weight of the composition may also be included. As known to those skilled in the art, the precise amount of thickeners can vary depending upon the consistency and thickness of the composition which is desired. Exemplary thickeners are xanthan gum, sodium carboxymethyl cellulose, hydroxyalkyl and alkyl celluloses (particularly hydroxypropyl cellulose), and cross-linked acrylic acid polymers such as those sold by B. F. Goodrich under the Carbopol trademark.

Collectively the water, solvents, silicones, esters, fatty acids, humectants and/or thickeners are viewed as pharmaceutically acceptable carriers for the sunscreen agents of the invention. Total amount of carrier will range from about 1 to 99.9%, preferably from about 80 to 99% by weight.

Cosmetic compositions of the present invention may be in any form. These forms may include lotions, creams, sticks, roll-on formulations, mousses, aerosol sprays and pad-applied formulations.

Surfactants may also be present in cosmetic compositions of the present invention. Total concentration of the surfactant will range from about 0.1 to about 40%, preferably from about 1 to about 20%, optimally from about 1 to about 5% by weight of the total composition. The surfactant may be selected from the group consisting of anionic, nonionic, cationic and amphoteric actives. Particularly preferred nonionic surfactants are those with a $C_{10}$–$C_{20}$ fatty alcohol or acid hydrophobe condensed with from about 2 to about 100 moles of ethylene oxide or propylene oxide per mole of hydrophobe; the $C_2$–$C_{10}$ alkyl phenols condensed with from 2 to 20 moles of alkylene oxide; mono- and di- fatty acid esters of ethylene glycol; fatty acid monoglyceride; sorbitan, mono- and di- $C_8$–$C_{20}$ fatty acids; and polyoxyethylene sorbitan as well as combinations thereof. Alkyl polyglycosides and saccharide fatty amides (e.g. methyl gluconamides) are also suitable nonionic surfactants.

Preferred anionic surfactants include soap, alkyl ether sulfate and sulfonates, alkyl sulfates and sulfonates, alkylbenzene sulfonates, alkyl and dialkyl sulfosuccinates, $C_8$–$C_{20}$ acyl isethionates and combinations thereof.

Compositions of the present invention may also contain $C_1$–$C_{20}$ α-hydroxycarboxylic acids and salts thereof. The salts are preferably alkalimetal, ammonium and $C_1$–$C_{12}$ alkanolammonium salts. Illustrative acids are glycolic acid, lactic acid and 2-hydroxycaprylic acid. Most preferred is a combination of glycolic and 2-hydroxycaprylic acids and their ammonium salts. Levels of these materials may range from about 0.01 to about 15%, preferably from about 0.1 to about 8%, optimally between about 0.1 and 1% by weight of the cosmetic composition.

Preservatives can desirably be incorporated into the cosmetic compositions of this invention to protect against the growth of potentially harmful microorganisms. Suitable traditional preservatives for compositions of this invention are alkyl esters of para-hydroxybenzoic acid. Other preservatives which have more recently come into use include hydantoin derivatives, propionate salts, and a variety of quaternary ammonium compounds. Cosmetic chemists are familiar with appropriate preservatives and routinely choose them to satisfy the preservative challenge test and to provide product stability. Particularly preferred preservatives are phenoxyethanol, methyl paraben, propyl paraben, imidazolidinyl urea, sodium dehydroacetate and benzyl alcohol. The preservatives should be selected having regard for the use of the composition and possible incompatibilities between the preservatives and other ingredients in the emulsion. Preservatives are preferably employed in amounts ranging from about 0.01% to about 2% by weight of the composition.

Minor adjunct ingredients may also be present in the cosmetic compositions. These ingredients include vitamins (such as Vitamin $B_6$, Vitamin C, Vitamin A palmitate, Vitamin E acetate, biotin, niacin and DL-panthenol). Particularly preferred is a combination of Vitamin C/polypeptide complex available as Vitazyme C from the Brooks Company, USA. Niacin, Vitamin $B_6$ and biotin are available from Roche Pharmaceuticals.

Another adjunct ingredient can be that of an enzyme. Particularly preferred is superoxide dismutase, commercially available as Biocell SOD from the Brooks Company, USA.

Natural vegetable materials from renewable resources are often desirable in cosmetic compositions. For instance, cosmetic compositions of the present invention may include β-glucan derived from oats, commercially available under the trademark Microat SF from Nurture Inc., Missoula, Mont. Another natural material is polymerized glucose with the CTFA name of sclerotium gum commercially available as Amigel® from Alban Muller International/Tri-K Industries, Inc., Emerson, N. J. Amounts of each of the foregoing materials may range from about 0.01 to about 10%, preferably from about 0.05 to about 1%, optimally between about 0.1 and 0.5% by weight.

Colorants, fragrances, opacifiers and abrasives may also be included in compositions of the present invention. Each of these substances may range from about 0.05 to about 5%, preferably between 0.1 and 3% by weight.

The following Examples will more fully illustrate the embodiments of this invention. All parts, percentages and proportions referred to herein and in the appended claims are by weight unless otherwise indicated.

EXAMPLE 1

A series of experiments were conducted to evaluate the SPF contribution from the EVA copolymer and microbeads of poly(methyl methacrylate). Table I sets forth the base composition as a fully formulated product, except without sunscreen.

In-vitro SPF of the formulated product with and without sunscreens was evaluated with an SPF-290 Analyzer, manufactured by Optometrics USA, Inc. of Ayer, Mass.

The optical system of the SPF-290 is comprised of a continuous UV-VIS source, color compensating filters, diffusion plates, a grating monochromator and detector. Ultraviolet (UVB) and near ultra-violet (UVA) radiation is provided by a Xenon arc lamp. The radiation emitted from the source is attenuated in such a way that it resembles the solar spectrum more closely. The beam of radiation reaches the sample and, at that point, is either transmitted, absorbed or reflected by the sample or substrate. Transmitted radiation passes through a series of diffuser plates which further attenuate it. The beam, then, enters a monochromator and, ultimately, the monochromatic radiation impinges on the photosensitive surface of the detector, generating a signal that is proportional to the intensity of the radiation striking the surface.

The method of measurement involved applying 80 microliters of sample unto a Transpore® tape supported by a holder. The sample was applied to an area of 6.4× 6.4 cm² in such a manner that a surface was covered approximating 40 cm². An amount of sample equal to 2 microliters per cm², which is similar to that used in standard in-vivo SPF tests, was distributed on the test tape. SPF measurements were then taken on the sample formulas.

Table II reports formulas A through H each of which utilizes the base composition but includes different amounts of organic sunscreen, EVA copolymer and/or PMMA. Table III reports sunscreen activity in terms of SPF values for the eight formulas.

TABLE I

| Base Composition | |
| --- | --- |
| COMPONENT | WEIGHT % |
| Carbopol 1382 ® (2% active) | 11.100 |
| Cyclomethicone | 6.000 |
| Isoarachidyl Neopentanoate | 5.300 |
| Isononyl Isononanoate | 2.500 |
| Arlacel 165 VS ® (GMS/PEG) | 1.700 |
| BRIJ 721 ® (Vegetable) | 1.200 |
| Isostearic Acid | 1.200 |
| Triethanolamine | 1.020 |
| Cetyl Alcohol | 1.000 |
| Actiglyde-J Special ® (Bio-hyaluronic acid) | 0.750 |
| Phenoxyethanol | 0.700 |
| Vitamin E Acetate | 0.500 |
| Algae Extract | 0.250 |
| BRIJ 72 ® (Vegetable) | 0.300 |

TABLE I-continued

| Base Composition | |
| --- | --- |
| COMPONENT | WEIGHT % |
| Methylparaben | 0.300 |
| Glydant ® | 0.200 |
| DL-Panthenol | 0.200 |
| $C_{12}$-$C_{20}$ Acid-PEG 8 Esters | 0.200 |
| Trilaureth-4-Phosphate | 0.200 |
| Silicone 200 (10cst) | 0.200 |
| Microat SF ® | 0.200 |
| Niacin | 0.200 |
| Vitazyme C ® | 0.100 |
| Superoxide Dismutase | 0.100 |
| Vitamin $B_6$ | 0.100 |
| Vitamin A Palmitate | 0.100 |
| Propylparaben | 0.100 |
| Amigel ® | 0.100 |
| Disodium EDTA | 0.100 |
| L-Lactic Acid | 0.010 |
| Biotin | 0.001 |
| Deionized Water | qs |

TABLE II

| SUNSCREEN COMPONENT | A | B | C | D | E | F | G | H |
| --- | --- | --- | --- | --- | --- | --- | --- | --- |
| Organic Sunscreen* | 7 | 7 | 7 | 7 | — | — | — | — |
| EVA Copolymer | — | 0.3 | 0.3 | — | 0.3 | 0.3 | — | — |
| PMMA | — | 1.0 | — | 1.0 | — | 1.0 | 1.0 | — |
| None (Base Composition) | 93 | 91.7 | 92.7 | 92 | 99.7 | 98.7 | 99 | 100 |

*5% Parsol MCX and 2% benzophenone-3

TABLE III

| SUNSCREEN ACTIVITY | A | B | C | D | E | F | G | H |
| --- | --- | --- | --- | --- | --- | --- | --- | --- |
| SPF | 24.7 | 34.2 | 24.2 | 23.8 | 1.5 | 1.3 | 1.1 | 1.1 |

SPF of the base composition with only organic sunscreen (formula A) is seen to increase from 24.7 to 34.2 in the presence of EVA copolymer and PMMA. See formula B which is representative of the present invention. Absent either the EVA copolymer or PMMA, as in formulas C and D respectively, the SPF again falls to around 24.

EXAMPLE 2

Another sunscreen composition according to the present invention is described in Table IV.

TABLE IV

| COMPONENTS | WEIGHT % |
| --- | --- |
| Ethylhexyl p-methoxycinnamate | 7.000 |
| Glycerin USP | 4.000 |
| Monaquat P-TS ® | 3.000 |
| Oxybenzone | 3.000 |
| Cetyl Alcohol | 2.500 |

TABLE IV-continued

| COMPONENTS | WEIGHT % |
| --- | --- |
| Octyl Palmitate | 2.000 |
| Glycerol Monostearate | 1.500 |
| Petroleum Jelly | 1.000 |
| Silicone Fluid | 1.000 |
| Covabead PMMA | 0.500 |
| EVA Copolymer | 0.500 |
| Quatrisoft LM-200 ® | 0.250 |
| Fragrance | 0.150 |
| Methyl Paraben | 0.150 |
| Propyl Paraben | 0.100 |
| Antifoam AF | 0.005 |
| Deionized Water | qs |
| TOTAL | 100.000 |

EXAMPLE 3

Another sunscreen composition according to the present invention is described in Table V. The formula is in lotion form.

TABLE V

| COMPONENT | WEIGHT % |
| --- | --- |
| Ethylhexyl p-Methoxycinnamate | 5.00 |
| Glycerin | 4.50 |
| Hetester PMA ® | 3.00 |
| Squalane | 2.80 |
| Isostearic Acid | 2.50 |
| Coco-Caprylate/Caprate (a blend of coco-caprylate and cococaprate) | 2.00 |
| Cyclomethicone | 2.00 |
| Benzophenone-3 | 2.00 |
| GMS/PEG-100 Stearate (a blend of glyceryl stearate and polyethylene glycol-100 stearate) | 2.00 |
| EVA Copolymer | 1.20 |
| Amerchol L-101 ® (A mixture of mineral oil and lanolin alcohol) | 1.00 |
| Cetyl Alcohol | 1.00 |
| Polyethylene 617 | 1.00 |
| DL-Panthenol | 1.00 |
| Covabead PMMA | 0.80 |
| Stearic Acid TP | 0.50 |
| Benzyl Alcohol | 0.50 |
| Vitamin E Linoleate | 0.50 |
| Germall 115 ® (Imidazolidinyl Urea) | 0.50 |
| Methylparaben | 0.30 |
| Triethanolamine | 0.30 |
| Cetearyl Alcohol | 0.25 |
| Solulan C-24 ® (Choleth-24 and Ceteath-24) | 0.25 |
| Glyceryl Stearate | 0.25 |
| Fragrance | 0.25 |
| Allantoin | 0.20 |
| Disodium EDTA | 0.20 |
| Propylparaben | 0.15 |
| Vitamin A Palmitate | 0.10 |
| Sodium Dehydroacetate | 0.10 |
| Xanthan Gum | 0.10 |
| Carbopol 941 ® | 0.10 |
| Tenox IV ® (A mixture of corn oil and BHA and BHT | 0.05 |
| Deionized Water | qs |

EXAMPLE 4

Another sunscreen composition according to the present invention is described in Table VI. The formula is in cream form.

TABLE VI

| COMPONENT | WEIGHT % |
| --- | --- |
| Octyl Methoxycinnamate | 7.00 |
| Hetester PMA ® | 3.00 |
| Cetyl Alcohol | 3.00 |
| Stearic Acid | 3.00 |
| Butylene Glycol | 3.00 |
| Cyclomethicone | 2.50 |
| 2-Hydroxy-4-Methoxybenzophenone | 2.00 |
| Cetyl Octanoate | 2.00 |
| Diisopropyl Adipate | 2.00 |
| Jojoba Oil | 2.00 |
| GMS/PEG 100 Stearate | 2.00 |
| Aluminum Starch Octenyl Succinate | 2.00 |
| EVA Copolymer | 1.20 |
| Polyethylene 617 | 1.00 |
| Nylon 12 | 1.00 |
| DL Panthenol | 1.00 |
| Butylene Glycol | 1.00 |
| Covabead PMMA | 0.80 |
| Benzyl Alcohol | 0.60 |
| Vitamin E Linoleate | 0.50 |
| Germall 115 ® | 0.50 |
| Cetearyl Alcohol | 0.50 |
| Glyceryl Stearte | 0.50 |
| Methylparaben | 0.30 |
| Triethanolamine 98% | 0.30 |
| Fragrance | 0.25 |
| Allantoin | 0.20 |
| Silicone Fluid 200, 100 cts | 0.20 |
| Disodium EDTA | 0.20 |
| Xanthan Gum | 0.20 |
| Ethylparaben | 0.15 |
| Vitamin A Palmitate | 0.10 |
| Sodium DHA | 0.10 |
| Carbopol 941 ® | 0.10 |
| Tenox IV ® | 0.05 |
| Deionized Water | qs |

The foregoing description and Examples illustrate selected embodiments on the present invention. In light thereof, various modifications will be suggested to one skilled in the art, all of which are within the spirit and purview of this invention.

What is claimed is:

1. A sunscreen composition comprising:
   (i) from about 0.01 to about 10% by weight of an ethylene/vinyl acetate copolymer;
   (ii) from about 0.01 to about 10% by weight of particles of an acrylic polymer derived from a monomer selected from the group consisting of ethyl acrylate, methyl acrylate, ethyl methacrylate, methyl methacrylate, butyl acrylate and butyl methacrylate;
   (iii) from about 0.1 to about 30% by weight of an organic sunscreen agent with a chromophoric group active within the ultraviolet radiation range from 290 to 400 nm; and
   (iv) from about 60 to about 99.5% by weight of a pharmaceutically acceptable carrier.

2. A composition according to claim 1 wherein the acrylic polymer is poly(methyl methacrylate).

3. A composition according to claim 1 wherein the acrylic polymer has an average particle size ranging from 0.001 to less than 5 microns.

4. A composition according to claim 1 wherein the acrylic polymer is present in an amount from about 0.8 to about 1.5% by weight.

5. A composition according to claim 1 wherein the ethylene/vinyl acetate copolymer is present in an amount from about 0.1 to about 2% by weight.

6. A composition according to claim 1 wherein water and oil are present to form an emulsion.

7. A composition according to claim 1 further comprising from about 0.01 to about 10% by weight of a β-glucan.

8. A composition according to claim 1 further comprising from about 0.01 to about 10% by weight of sclerotium gum.

* * * * *